United States Patent
Möllstam

(10) Patent No.: US 7,661,582 B2
(45) Date of Patent: Feb. 16, 2010

(54) MEDICAL INDICATION DEVICE AND IDENTIFICATION METHOD

(75) Inventor: Anders Möllstam, Saltsjö-boo (SE)

(73) Assignee: Medical Vision Research & Development AB., Nacka (SE)

( * ) Notice: Subject to any disclaimer, the term of this patent is extended or adjusted under 35 U.S.C. 154(b) by 627 days.

(21) Appl. No.: 10/530,409

(22) PCT Filed: Oct. 9, 2003

(86) PCT No.: PCT/SE03/01574

§ 371 (c)(1),
(2), (4) Date: Aug. 2, 2005

(87) PCT Pub. No.: WO2004/033024

PCT Pub. Date: Apr. 22, 2004

(65) Prior Publication Data

US 2006/0058804 A1    Mar. 16, 2006

(30) Foreign Application Priority Data

Oct. 10, 2002  (SE) .................................. 0202991

(51) Int. Cl.
*G06F 17/00* (2006.01)
(52) U.S. Cl. .................. 235/375; 235/376; 235/439
(58) Field of Classification Search ............... 235/375, 235/376, 439, 451, 454, 462.01, 462.13, 235/462.14, 462.43, 485, 486, 492
See application file for complete search history.

(56) References Cited

U.S. PATENT DOCUMENTS

| 5,078,683 | A | 1/1992 | Sancoff et al. |
| 5,131,823 | A | 7/1992 | Guignard |
| 5,591,344 | A * | 1/1997 | Kenley et al. ............... 210/636 |
| 6,626,355 | B2 * | 9/2003 | Sasse et al. .................. 235/375 |
| 7,108,184 | B2 * | 9/2006 | Mase et al. ............ 235/462.01 |
| 7,299,981 | B2 * | 11/2007 | Hickle et al. ................ 235/385 |
| 2001/0020148 | A1 * | 9/2001 | Sasse et al. ................... 604/65 |
| 2002/0188259 | A1 * | 12/2002 | Hickle et al. ................ 604/189 |

FOREIGN PATENT DOCUMENTS

| DE | 198 22 751 A 1 | 9/1999 |
| EP | 1 101 506 A2 | 5/2001 |
| WO | 93/05829 A1 | 4/1993 |
| WO | WO 93/05829 | 4/1993 |
| WO | 01/74421 A1 | 10/2001 |
| WO | WO 01/74421 A1 | 10/2001 |

OTHER PUBLICATIONS

International Search Report dated Dec. 5, 2003, at the Swedish Patent Office.

* cited by examiner

*Primary Examiner*—Daniel A Hess
*Assistant Examiner*—Paultep Savusdiphol
(74) *Attorney, Agent, or Firm*—Lynn E. Barber

(57) ABSTRACT

The present invention relates to a medical-technical identification device for identifying a sterile product (4, 62, 72, 82), and to a method of identifying such a product, for example a product intended for one-time-use only, when connected to a piece of medical equipment (1, 60, 70, 80), wherein the sterile product (4, 62, 72, 82) includes a fixedly mounted information carrier (9, 63, 73, 83) which is adapted to deliver or to offer specific product information in a contactless fashion to a reading element (12, 64, 74, 84) connected to the equipment (1, 60, 70, 80).

8 Claims, 2 Drawing Sheets

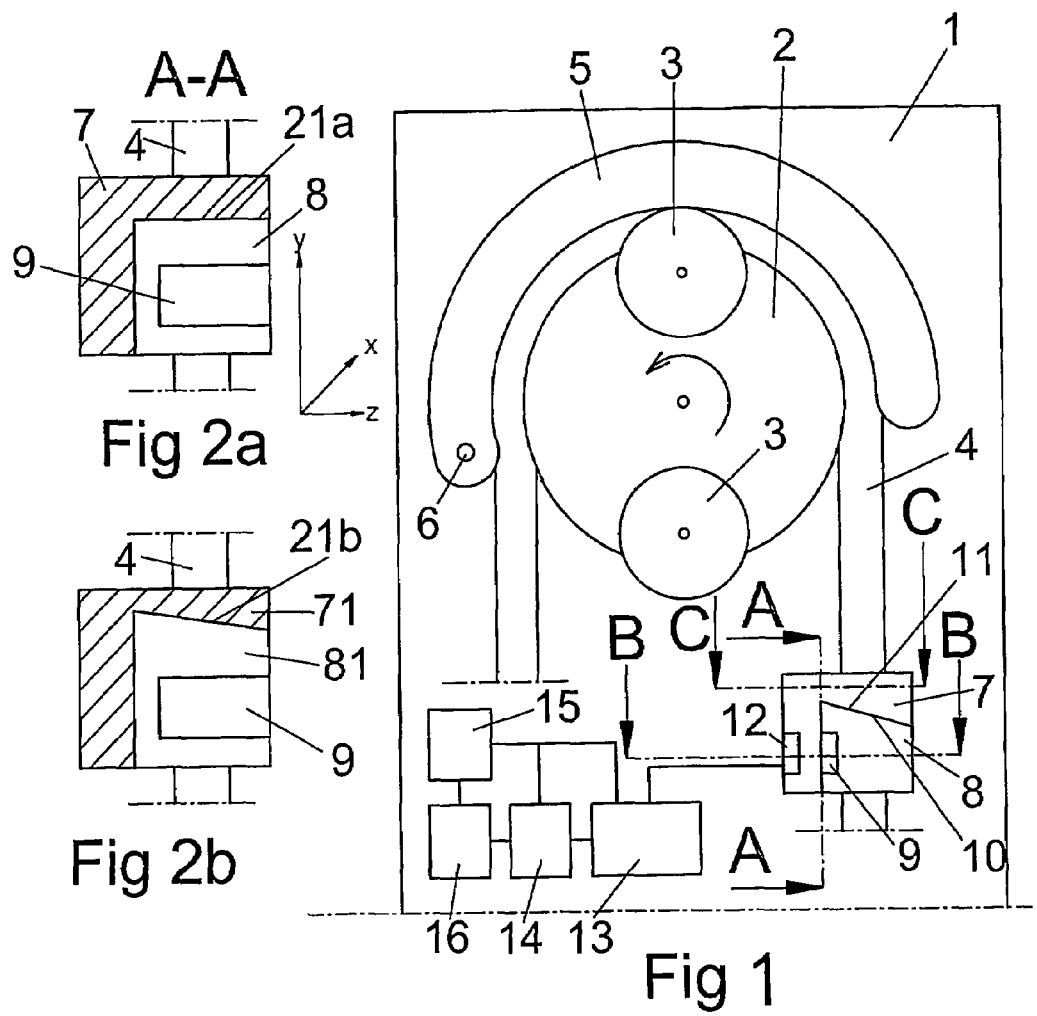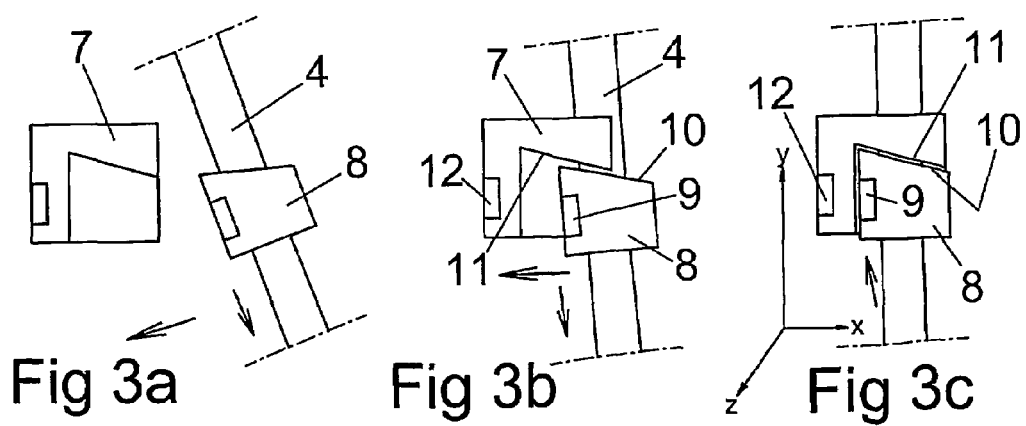

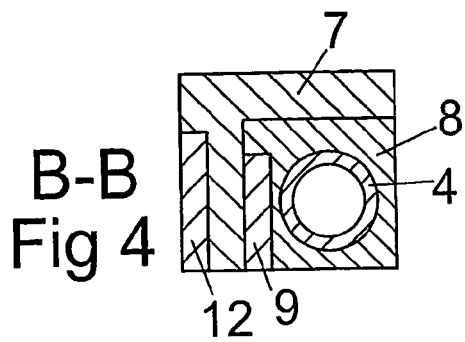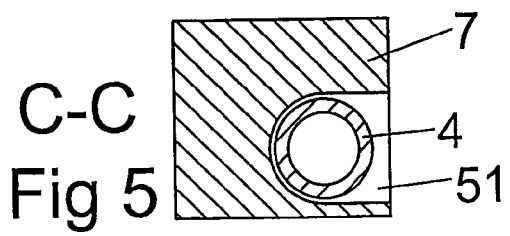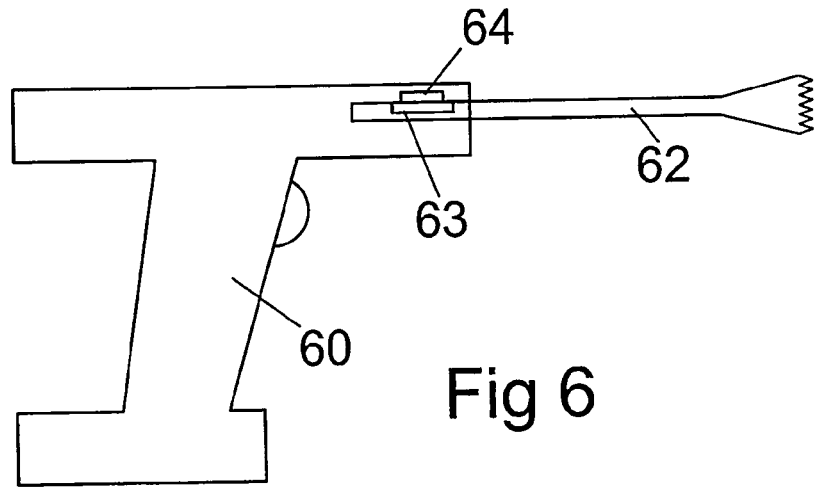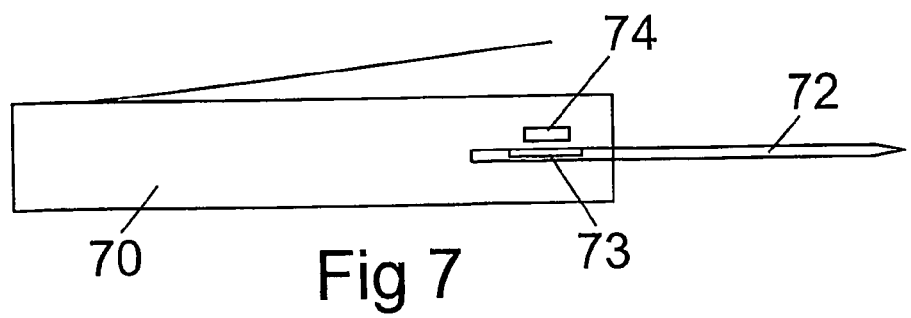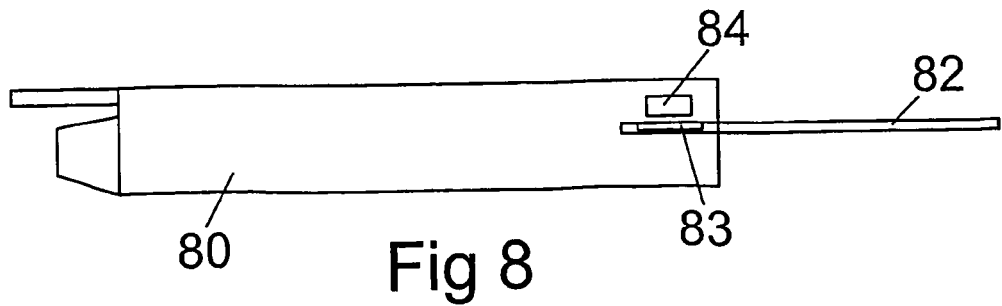

MEDICAL INDICATION DEVICE AND IDENTIFICATION METHOD

This application is the US national phase of international application PCT/SE2003/001574 filed 9 Oct. 2003 which designated the U.S. and claims benefit of SE 0202991-6, dated 10 Oct. 2002, the entire contents of each of which are hereby incorporated by reference.

FIELD OF INVENTION

The identification device pertains to the medical field and then particularly to the field in which sterile products shall be connected together and in which it is of paramount importance that the correct parts are connected, for instance when part of a hose shall be connected to an infusion-type fluid pump.

BACKGROUND OF THE INVENTION

U.S. Pat. No. 5,131,823 makes known a device for joining a connection piece to peristaltic pump. As evident from the descriptive part of the document, one end of a hose is provided with a sleeve for connection to an end of a further hose. The connection sleeve includes a disc-shaped angled collar which is intended to be received in a slot disposed in a support device and facing towards the disc. The sleeve together with its angled disc functions to fixate the hose ends in a correct position relative to the peristaltic pump. Moreover, the angled disc causes an increase in tension forces caused by the pump to result in a self-locking action by virtue of the sleeve being pressed against a seat.

One problem with this device is that hoses can be mixed-up, even when color-marked. Furthermore, unintentional confusion between the hoses can go as far as causing the equipment to be used wrongly in the absence of any indication to the contrary.

OBJECT OF THE INVENTION

The object of the present invention is to eliminate the aforesaid problems by identifying that the correct coupling elements have been joined together, and to prevent a piece of equipment from functioning when coupling the wrong product to said equipment, and to record a product history.

Another object is to enable a sterile medical product to be checked to ensure that it is connected to the correct equipment or appliance, in other words to the equipment delivered by the supplier or manufacturer and approved for the product concerned.

A further object is to enable a check to be made to ensure that products intended for one-time use only are not connected to said equipment more than once.

Still another object is to enable the use of a sterile one-time-only product to be stopped when this product has been withdrawn/stopped by the manufacturer or has passed its expiry date with respect to its sterility.

Yet another object is to enable programming of a time interval over which the product can be used in a piece of equipment, possibly even more than once if sterility of the product is maintained.

SUMMARY OF THE INVENTION

These objects are achieved by means of the present invention as defined in the accompanying independent claims.

Suitable further embodiments of the invention will be apparent from the accompanying dependent claims.

The invention relates to an identification device whose purpose is to identify the correct connection of a sterile product to a piece of medical equipment and/or that the correct product has been connected, for instance that a hose is of the correct type for the use given, and to indicate the number of times that the sterile product has been used and therewith signal for service, stoppage or replacement of equipment. The identification device also includes a processor-controlled storage unit and a control unit for controlling the medical equipment in response to information obtained from the hose for instance. Identification is achieved through the medium of an information carrier connected to the hose and programmed with hose-relevant information, such as approved use, lot number, batch number, hose dimensions, elasticity, and manufacturer, all of this information being programmed in the information carrier either in connection with or subsequent to manufacture.

A reading element, a receiver, receives the information programmed in the identification device, the transmitter, and permits the information to be further processed so as to enable the equipment, e.g. the infusion pump, to be controlled or shut down entirely in response to the absence of information or in response to erroneous information. The invention thus adds a measure of security with regard to the connection of the correct appliance said equipment.

The information carrier is fitted fixedly in, e.g., a holder which is fixed to the hose and which includes an oblique surface as seen in the direction in which the hose is pulled. The surface has an angle of 30°-70°, preferably 45°, in relation to said direction. The surface co-acts with a fixation seat fixedly mounted on said equipment and corresponding to said surface. In fitting the hose to an infusion pump, one end of the hose is fitted to the pump in a conventional manner and the hose is extended around an impeller and stretched elastically with its holder positioned over said seat, wherewith the resultant elasticity of the hose causes the surfaces to slide against each other. When sliding of the surfaces ceases, the information carrier and the reading element will be in mutual alignment such as to obtain maximum transmission quality.

An identification check is carried out with the aid of an information carrier mounted in a sterile medical article, e.g. an article intended for one-time-use only, and containing unique identification information which is read by a reading element mounted in a medical apparatus. The information is registered in the device and can then be used in respect of the following procedures, among other things:

1. The receiver ascertains whether or not the article coupled to the medical apparatus has been approved. The apparatus may be programmed to shut down if the article is found not to be approved, therewith avoiding an accident. An example of a non-approved article may be that
   the article has been stopped, for instance its batch number/lot number has been withdrawn by the manufacturer,
   the article has passed its sterility date
   the article is about to be reused. The article can be allowed to be connected to an apparatus several times, although within a limited time period, e.g. within a 24 hour period.
2. Stored as a file document, e.g. on the hard disk of a computer. This stored information can then be retrieved to
   show for how long articles have been connected to the apparatus.
   show how often the apparatus has been used, for instance how often the article has been connected up during a given time interval. The information can be used to inform the user of the extent to which the apparatus has been in use, i.e. to optimise the degree of use, to inform the user when it is appropriate to send the apparatus away for service.

Data is programmed in the information carrier during or after manufacture of the product. The reading element is controlled by software, and, for instance, service intervals can be programmed in.

The invention is comprised of a medical-technical identification device for identifying sterile products, e.g. products intended for one-time-use only, when connected to medical equipment. The sterile product has fixedly attached thereto an information carrier which is adapted to deliver specific product information to a reading element connected to said equipment or to provide the reading element with such information, in a contactless fashion. The information carrier is a passive component and may therewith have the nature of a smart card. The sterile product may particularly consist in an elastic hose-part. In the case of one embodiment, the information carrier is mounted in a holder and the reading element is mounted in a fixating seat. The exchange of information between the information carrier and the reading element does not take place until said hose-part has been fully connected to the equipment. In one embodiment the information carrier and the reading element are adapted to take a fixed position relative to one another when said hose part is connected actively to the equipment. In one embodiment the holder of the information carrier includes a planar slide surface that defines an angle in accordance with the aforesaid, such that the normal to the surface will not extend parallel to the symmetry axis of said hose part and such that said slide surface will fit with a correspondingly orientated slide surface in the fixation seat. In one embodiment both slide surfaces are directed so that a force applied to press the surfaces against each other will cause the information carrier and the reading element to be brought into mutual alignment in the X-direction and the Y-direction. In one embodiment the two slide surfaces are directed so that the information carrier and the reading element will also be brought into alignment in the Z-direction.

The reading element is connected to a register which, in turn, is connected to both a storage unit and to an analysing unit. The analysing unit sends signals to a control unit which is adapted to bring influence to bear on the equipment. The arrangement also includes a presentation unit which functions to show information from both the analysing unit and the storage unit. Also included is a programming unit, which is connected to one of said units.

The transfer of information between the information carrier and the reading element is effected through the medium of one or more of the following devices:

bar code, Blue tooth, radio waves, light waves—e.g. infrared light, electromagnetism, radioactivity, or chemical transmission.

The invention also relates to a method of identifying a sterile product, e.g. a product intended for one-time-use only, connected to medical equipment, wherein a reading element connected to the equipment receives specific product information from an information carrier fixedly mounted on the product, in a contactless fashion, and wherein the information received is compared with predetermined criteria so as to bring influence to bear on the equipment if the criteria are not fulfilled.

Although the following description is concentrated on a hose as the product and on an infusion pump as medical equipment, it will be understood that the present invention is particularly suitable with regard to other products and other pieces of equipment within the medical-technical field where high safety requirements with regard to sterility prevail.

BRIEF DESCRIPTION OF THE DRAWINGS

The invention will now be described in more detail with reference to exemplifying embodiments thereof and also with reference to the accompanying drawings, in which FIG. 1 illustrates an embodiment of an inventive identification device;

FIG. 2a is a sectional view of a first embodiment of the inventive device shown in FIG. 1, said view being taken on the line A-A in FIG. 1;

FIG. 2b is a sectional view of a second embodiment of the invention according to FIG. 1 taken on the line A-A;

FIGS. 3a-c illustrate a sequence of manual operations undertaken in securing a hose in accordance with the invention;

FIG. 4 is a sectional view taken on the line B-B in FIG. 1;

FIG. 5 is a sectional view taken on the line C-C in FIG. 1;

FIG. 6 is a schematic view of an oscillating saw in accordance with the invention;

FIG. 7 is a schematic view of a drill in accordance with the invention; and

FIG. 8 is a schematic view of a shaver in accordance with the invention.

DESCRIPTION OF THE INVENTION

FIG. 1 is a schematic illustration of an infusion pump 1 that includes a pump hose connecting device in accordance with the invention. The pump 1 also includes an impeller 2 which, in turn, includes two press wheels 3 which are intended to press a hose 4 against an arrestor 5 located in the pump. The hose part 4 is fitted to the pump 1 in the following manner: The arrestor 5 is raised about its mounting shaft 6, wherewith the impeller 2 acts as a bending means around which the part 4 of the hose is placed. One end of the hose part 4 is herewith fastened to the medical equipment, that is to the infusion pump 1, in a conventional manner. The hose part 4 is then tensioned around the impeller 2 and stretched elastically into a position beneath a fixation seat 7 and fastened in this position. The seat 7 is fixedly connected to the pump 1. A holder 8 is fixedly connected to the hose part 4 in the region of the fixation seat 7, said holder being provided with an information carrier 9. In the case of the illustrated embodiment the holder 8 has the form of an alignment block that includes an upper oblique surface 10 which conforms to a corresponding oblique surface in the seat 7. The holder 8 is shown mounted in the seat 7 in the Figure, with the information carrier on the holder located opposite a reading element 12 disposed in the seat 7. As will be seen from the Figure, the reading element 12 is connected to a register 13 which, in turn, is connected to a storage unit 14 on the one hand and to an analysing unit 15 on the other hand. The storage unit is also connected directly to the analysing unit. A presentation unit 16 is connected directly to both the analysing unit 15 and the storage unit 14. Depending on the nature of the information delivered from the information carrier 9 and checked in the analysing unit 15, a control unit (not shown) is actuated to either approve the connection of the hose part 4 to said equipment or to stop continued functioning of the pump 1.

FIGS. 2a and 2b are sectional views taken on the line A-A in FIG. 1, FIG. 2a illustrating a first embodiment and FIG. 2b a second embodiment. The embodiment according to FIG. 2a includes a holder 8 which is actively mounted in the seat 7 by virtue of its upper edge surface 21a being in abutment with a corresponding edge surface in the seat 7. In this case, the edge surface 21a is horizontally disposed, i.e. at right angles to the symmetry axis of the hose part 4, wherewith a pulling force applied upwardly to the hose part 4 in the Figure will bring the holder into alignment in the direction of the X and Y axes respectively in accordance with the coordinate system shown in FIG. 2a. This alignment of the holder in said X and Y directions respectively results in the alignment of the information carrier 9 in the holder 8 in two mutually perpendicular directions relative to the reading element 12.

FIG. 2b illustrates a second embodiment of a holder, 81, fitted in a fixation seat, 71. In this embodiment the upper edge surface, 21b, of the holder 81 is inclined inwardly of the seat 71 so that a pulling force applied upwardly on the hose part 4 in the Figure will result in the alignment of holder 81 also in the Z-direction in accordance with the coordinate system shown in FIG. 2a. This embodiment thus provides alignment of the information carrier 9 in all three mutually perpendicular directions X, Y and Z.

FIGS. 3a-3c illustrate a sequence of events in fitting the holder 8 applied to the hose part 4 in the fixation seat 7. After having secured the equipment-fixed end of the hose part 4 in the infusion pump, the hose part 4 is drawn over the impeller 2, wherewith the arrestor 5 snaps down and locks in the position shown in FIG. 1. The hose part 4 is then stretched down in FIG. 3, wherewith the holder 8 reaches a position in which it can be snapped into the seat 7, in accordance with the arrows in FIG. 3a.

FIG. 3b shows a state in which the hose part 4 has been brought closer in towards the seat 7. It will be seen that respective slide surfaces 10 and 11 in the holder 8 and the seat 7 are so angled in relation to each as to bring the information carrier 9 and the reading element 12 into alignment with one another.

FIG. 3c shows the device in its finally assembled state, although a small gap has been left around the holder 8 so that the positions of the surfaces 10, 11 and the information carrier 9 and the reading element 12 can be seen clearly. The Figure also shows the orthogonal coordinate system illustrated in FIG. 2a.

FIG. 4 is a sectional view of the identification device taken on the line B-B in FIG. 1. It will be seen that the hose part 4 is firmly fixed in the holder 8 and that an information carrier 9 is inserted into the holder. It will also be seen that the holder is fitted in the seat 7 and that the information carrier 9 is situated opposite the reading element 12, which is also inserted into the seat 7.

FIG. 5 is a sectional view taken on the line C-C in FIG. 1. As will evident from the Figure, the end of the hose part 4 is inserted into the seat 7 through an open slot 51 provided on one side thereof.

FIG. 6 shows another medical application for identifying a sterile product. This application relates to the use of an orthopaedic oscillating saw 60 to which there has been connected a sterile saw blade 62 that carries an information carrier 63. The information carrier 63 will be located opposite a reading element 64 when the saw blade 62 has been fitted, said information carrier 63 and said reading element 64 being adapted to operate in a manner corresponding to that earlier described.

FIG. 7 illustrates a further application of the present invention. This application is concerned with the handgrip 70 of an orthopaedic drill to which there is fitted a sterile drill bit 72 that carries an information carrier 73. As in the earlier case, the information carrier 73 is also adapted to deliver or to offer specific product information to a reading element 74 connected to the handgrip 70.

A further embodiment is shown in FIG. 8. In this embodiment a shaver handgrip 80 has fitted thereto a sterile shaver blade 82 which, similar to the embodiments described in the foregoing, includes an information carrier 83 which, when the shaver blade 82 is fitted, is located opposite a reading element 84.

It will be understood that other embodiments within the medical-technical field are conceivable within the scope of the invention, where a sterile product is connected to sterile medical equipment in a manner to ensure that sterility will not be lost and that safety can be maintained.

The invention claimed is:

1. A medical-technical identification device for identifying a sterile product that is intended for a one-time-use only, when connected to a piece of medical equipment, the identification device comprising:

a holder fixedly connected to the sterile product, the holder including a first oblique slide surface, as seen in the direction in which the sterile product is mounted, an information carrier fixedly attached to the holder, which is adapted to deliver, or to offer specific product information in a contactless fashion, a seat fixedly mounted on the piece of medical equipment, the seat including a second oblique slide surface, as seen in the direction in which the sterile product is mounted, a reading element that is connected to the seat and to a registering unit which, in turn, is connected to both a storage unit and an analysing unit, the information carrier being mounted in a fixed relation to the first oblique slide surface wherein the first oblique slide surface and the second oblique slide surface are angled so that when the holder is fitted within the seat, the first oblique slide surface and the second oblique slide surface are brought directly together, placing the information carrier and the reading element into contactless alignment with one another, the sterile product being a sterile elastic hose part, a sterile saw blade, a sterile drill bit, or a sterile shaver blade, the analysing unit functioning to deliver signals to an equipment actuating control unit, the device further comprising a presentation unit which functions to present information from both the analysing unit and the storage unit, and a programming unit connected to the analysing unit or the storage unit, wherein bringing the information carrier and the reading element into contactless alignment with one another enables identifying of the sterile product.

2. An identification device according to claim 1, characterised in that the information carrier is mounted in or on one side of a holder and in that the reading element is mounted in or on one side of the fixation seat, wherein the exchange of information between the information carrier and the reading element does not take place until the holder is in place in the seat, until connection of the hose part to the equipment has been completed.

3. An identification device according to claim 2, characterised in that the information carrier and the reading element are adapted to take fixed positions relative to one another when the hose part is connected actively to said equipment.

4. An identification device according to claim 3, characterised in that the holder of the information carrier includes a planar slide surface which is angled such that the normal to said surface will not extend parallel with the symmetry axis of said hose part and in that said slide surface conforms to or fits with a correspondingly directed slide surface in the seat.

5. An identification device according to claim 4, characterised in that both slide surfaces are directed so that an applied force intended to press the surfaces together will cause the information carrier and the reading element to be aligned mutually in the direction of an X-axis and Y-axis.

6. An identification device according to claim 5, characterised in that both slide surfaces are directed so that the information carrier and the reading element will also be mutually aligned in the direction of an Z-axis.

7. An identification device according to claim 1, characterised in that the transmission of information between the information carrier and the reading element is caused to take place with the aid of one or more of the following devices: bar codes, Blue Tooth, radio waves, light waves, infrared light, electromagnetism, radioactivity or chemical transmission.

8. A device for identifying a sterile product that is intended for a one-time-use only, when the sterile product is connected to a piece of medical equipment, the device comprising:

a reading element for receiving or reading product information for products connected to the piece of medical equipment, an information carrier mounted in a fixed relation to a first oblique slide surface, as seen in the direction in which the sterile product is mounted, of the sterile product and adapted to deliver, or to offer specific product information in a contactless fashion to the reading element, and a seat, configured to receive the information carrier, fixedly mounted on the piece of medical equipment, the seat including the reading element and a second oblique slide surface, as seen in the direction in which the sterile product is mounted, with which the first oblique slide surface co-acts directly when the sterile product is connected to the piece of medical equipment, the second oblique slide surface corresponding to the first oblique slide surface so as to bring the information carrier and the reading element into contactless alignment with one another, wherein bringing the information carrier and the reading element into contactless alignment with one another enables identifying of the sterile product.

* * * * *